United States Patent
Kotake et al.

(10) Patent No.: US 7,935,395 B2
(45) Date of Patent: May 3, 2011

(54) LIQUID CRYSTAL MOLECULE, LIQUID CRYSTAL DISPLAY DEVICE AND LIQUID CRYSTAL OPTICAL SPATIAL MODULATION DEVICE

(75) Inventors: Rika Kotake, Kanagawa (JP); Hidehiko Takanashi, Kanagawa (JP); Ken Kobayashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 10 days.

(21) Appl. No.: 12/573,182

(22) Filed: Oct. 5, 2009

(65) Prior Publication Data

US 2010/0085530 A1    Apr. 8, 2010

(30) Foreign Application Priority Data

Oct. 8, 2008    (JP) ............... P2008-261261

(51) Int. Cl.
| | |
|---|---|
| *C09K 19/32* | (2006.01) |
| *C09K 19/30* | (2006.01) |
| *C09K 19/34* | (2006.01) |
| *C09K 19/20* | (2006.01) |
| *G02F 1/133* | (2006.01) |
| *C07F 7/04* | (2006.01) |
| *C07F 7/08* | (2006.01) |
| *C07F 7/10* | (2006.01) |
| *C07F 7/18* | (2006.01) |

(52) U.S. Cl. ............... 428/1.1; 252/299.61; 252/299.62; 252/299.63; 252/299.67; 349/184; 556/407; 556/418; 556/422; 556/425; 556/434; 556/450; 556/451; 556/452; 556/453; 556/454

(58) Field of Classification Search ............. 252/299.61, 252/299.62, 299.63, 299.67; 349/184; 556/407, 556/418, 422, 425, 434, 437, 450, 451, 452, 556/453, 454; 428/1.1
See application file for complete search history.

(56) References Cited

U.S. PATENT DOCUMENTS

| | | | | |
|---|---|---|---|---|
| 5,072,021 | A * | 12/1991 | Nakatsuka et al. | 560/56 |
| 5,106,530 | A * | 4/1992 | Haas et al. | 252/299.6 |
| 5,329,034 | A * | 7/1994 | Nagase et al. | 556/415 |
| RE35,462 | E * | 2/1997 | Haas et al. | 252/299.6 |
| 6,300,454 | B1 * | 10/2001 | Hanelt et al. | 528/27 |
| 7,615,165 | B2 * | 11/2009 | Takanashi | 252/299.01 |
| 2008/0143950 | A1 | 6/2008 | Takanashi et al. | |

FOREIGN PATENT DOCUMENTS

| | | |
|---|---|---|
| DE | 195 22 195 | 6/1995 |
| JP | 63-233932 | 9/1988 |
| JP | 04-029993 | 1/1992 |
| JP | 05-105686 | 4/1993 |
| JP | 2008-150334 | 7/2008 |

OTHER PUBLICATIONS

Stephen Garoff and Robert B. Meyer; Electroclinic Effect at the A-C Phase Change in a Chiral Smectic Liquid Crystal; Physical Review Letters; vol. 38, No. 15; Apr. 11, 1977.

J. Naciri et al.; Novel Ferroelectric and Electroclinic Organosiloxane Liquid Crystals; Chem. mater; 1995, 7; 1397-1402.

Japanese Office Action issued on Sep. 28, 2010 in connection with counterpart JP Application No. 2008-261261.

* cited by examiner

*Primary Examiner* — Shean C Wu
(74) *Attorney, Agent, or Firm* — SNR Denton US LLP

(57) ABSTRACT

A liquid crystal molecule is disclosed, having a structure represented by the following general formula (1):

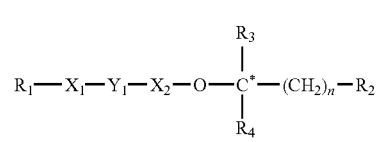

wherein
$X_1$ is a group selected among groups represented by the following formula (2):

(2)

$X_2$ is represented by the following formula (3):

(3)

$R_1$ represents a linear or branched hydrocarbon group or an alkoxy group each having from 4 to 16 carbon atoms;

$R_2$ represents an optionally branched organosiloxane or organosilane having from 1 to 6 silicon atoms;

other variables in formulae are defined therein.

4 Claims, 3 Drawing Sheets

LIQUID CRYSTAL MOLECULE, LIQUID CRYSTAL DISPLAY DEVICE AND LIQUID CRYSTAL OPTICAL SPATIAL MODULATION DEVICE

BACKGROUND OF THE INVENTION

1. Field of the Invention

The present invention relates to a liquid crystal molecule and to a liquid crystal display device and a liquid crystal optical spatial modulation device each using the liquid crystal molecule.

2. Description of the Related Art

In recent years, a liquid crystal display device (LCD) of an active matrix driving type such as a TFT (thin film transistor) has been widely used over the range of from small mobile uses to large television sets.

In the LCD, techniques such as impulse driving have been being adopted, thereby attempting to realize a high response speed. However, it is the actual situation that the LCD is inferior to a plasma display (PDP), a field emission display (FED) and the like in display quality regarding dynamic images due to, for example, dynamic image blur to be caused by a slow response speed of a liquid crystal material itself.

Meanwhile, attempts have also been being made to increase a speed of the current 60 Hz frame rate drive to 120 Hz or 240 Hz (high frame rate drive), thereby enhancing the dynamic image display quality. Though the dynamic image display quality in the LCD partly depends upon the driving system including a TFT, it depends mostly on the response characteristics of the liquid crystal material itself. Namely, the foregoing problem may not radically be solved, and the high frame rate drive may not be realized, unless the liquid crystal material is responsible to a high speed.

In the light of the above, it is the situation that a liquid crystal material which can cope with the high frame rate drive and which can exhibit high-speed response permitting realization of a high dynamic image display quality is keenly demanded.

As a liquid crystal capable of realizing high-speed response, a nematic liquid crystal attended by a flexoelectric effect, a ferroelectric liquid crystal, an antiferroelectric liquid crystal and the like are known. The present inventors have paid attention to an electroclinic effect in a smectic A phase.

The electroclinic effect is a phenomenon in which in a smectic A phase, optical axes of liquid crystal molecules uniaxially aligned (liquid crystal molecule longitudinal axes) are inclined according to an intensity of an impressed electric field (see Garoff, et al., *Physical Review Letters*, Vol. 38, 1977, page 848). When this type of cell is disposed between orthogonal polarizing plates, a transmitted light quantity according to an angle (tilt angle) formed by an optical axis of the polarizing plate and an optical axis of the liquid crystal is obtained (see the following expression (A)), and a maximum transmittance is obtained at a tilt angle of ±45°.

$$T/T_0 = \sin^2(2\theta) \times \sin^2(n\Delta nd/\lambda) \tag{A}$$

Here, T represents a transmitted light quantity; $T_0$ represents an incident liquid quantity; $\theta$ represents an angle (tilt angle) formed an optical axis of the polarizing plate and an optical axis of the liquid crystal; $\Delta n$ represents a birefringence of the liquid crystal; d represents a thickness of the liquid crystal layer; and $\lambda$ represents a wavelength of the transmitted light.

Figure 6:
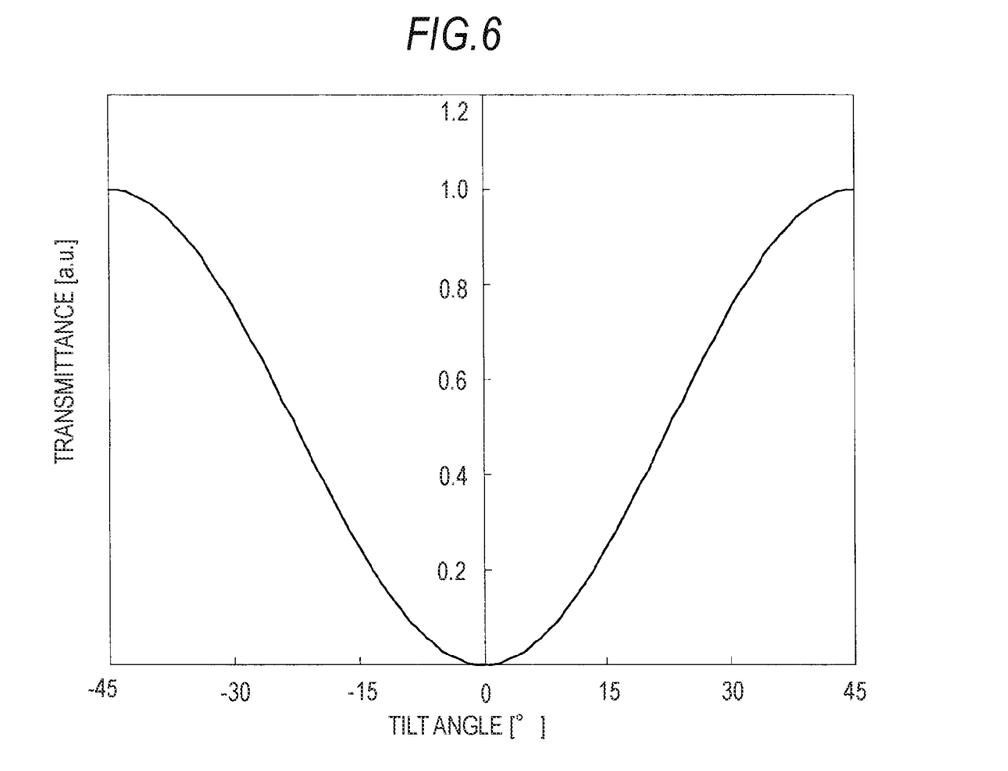
FIG. 6 is a diagram showing the relationship between a tilt angle and a transmittance in a liquid crystal cell having aligned uniaxially liquid crystal molecules which display a smectic A phase.

Results obtained by calculating the dependency of the transmittance on the tilt angle in case of a retardation ($=\Delta nd$) giving a maximum transmittance according to the foregoing expression (A) are shown in FIG. 6.

A response time in the electroclinic effect is very fast as from several μseconds to several tens μseconds. Also, there is a merit that in a low electric field intensity, an inclination angle (tilt angle) of the optical axis is proportional (i.e., voltage modulation of transmitted light is possible). That is, it may be said that this is a display mode which is very suited for the active matrix driving.

However, the tilt angle which has hitherto been revealed in liquid crystal materials is not so large that sufficient optical modulation is not obtainable yet.

As a liquid crystal material displaying a large tilt angle, a material system in which a siloxane is added to a non-chiral end is known. A reason for this may be considered to reside in the fact that such a siloxane has a larger volume than that of usual alkyl chains, and when a flexible functional group is added to a terminal group, a core portion which contributes to the optical modulation becomes easily movable by the action of an electric field. According to Naciri, et al., *Chem. Mater.*, 1995, 7, pages 1397 to 1402, in case of a liquid crystal molecule having a structure in which a siloxane is added to a non-chiral end, a maximum tilt angle of 26° is obtained. However, according to the foregoing expression (A), the transmittance is about 60% at the most. Also, since a nitro group is introduced as a polarizing group, the polarization is large. Thus, such a liquid crystal material is still insufficient in consideration of putting a display device or the like into practical use.

Furthermore, JP-A-2008-150334 discloses a liquid crystal molecule having a structure having an asymmetric carbon atom and having a core portion including a plurality of aromatic groups and an organosiloxane at positions opposite to each other interposing the asymmetric carbon atom therebetween. However, this liquid crystal molecule is not sufficiently satisfactory in view of the fact that a tilt angle is small, and a more increase of the tilt angle is desirable.

SUMMARY OF THE INVENTION

It is desirable to provide a liquid crystal molecule having a large tilt angle in an electroclinic effect and capable of obtaining sufficient optical modulation.

Also, it is desirable to provide a liquid crystal display device and a liquid crystal optical spatial modulation device each using a liquid crystal molecule having a large tilt angle in an electroclinic effect and capable of obtaining sufficient optical modulation.

The present inventors have found that the tilt angle can be further increased by a compound having a structure having an asymmetric carbon atom and having a core portion including naphthylene group containing a functional group and an organosilane or an organosiloxane at positions opposite to each other interposing the asymmetric carbon atom therebetween and made extensive and intensive investigations on the basis of this finding, leading to accomplishment of the present invention.

According to an embodiment of to the present invention, there is provided a liquid crystal molecule having a structure represented by the following general formula (1).

(1)

In the general formula (1), $X_1$ is a group selected among groups represented by the following formula (2).

(2)

In the general formula (1), $X_2$ is represented by the following formula (3).

(3)

In the formulae (1) to (3), $R_1$ represents a linear or branched hydrocarbon group or an alkoxy group each having from 4 to 16 carbon atoms; $R_2$ represents an optionally branched organosiloxane or organosilane having from 1 to 6 silicon atoms; and $R_3$ and $R_4$ are different from each other and each represents H, F, Cl, Br, CN, $CH_3$, $CF_3$ or $OCH_3$.

$Y_1$ represents -, —COO—, —$CH_2$—, —$CH_2O$—, —$C_2H_2$—, —$C_2$— or —$CF_2O$—.

$Z_1$ to $Z_4$ each represents H, F, Cl, Br, OH, $NO_2$, CN, $CF_3$, $CH_3$, $C_2H_5$, $OCH_3$ or $OC_2H_5$; $Z_5$ to $Z_7$ each represents H, F, Cl, Br, OH, $NO_2$, CN or $CF_3$, provided that $Z_5$, $Z_6$ and $Z_7$ do not represent H at the same time.

n represents an integer of from 1 to 6; * represents a chiral center; and - means a connecting group.

According to another embodiment of the present invention, there is provided a liquid crystal molecule having a structure represented by the following general formula (4).

(4)

In the general formula (4), $X_2$ is represented by the following formula (3).

(3)

In the formulae (3) and (4), $R_{11}$ represents a linear or branched alkoxy group having from 4 to 16 carbon atoms; and $R_{13}$ represents F, Cl, Br, CN, $CH_3$, $CF_3$ or $OCH_3$.

$Z_1$ to $Z_4$ each represents H, F, Cl, Br, OH, $NO_2$, CN, $CF_3$, $CH_3$, $C_2H_5$, $OCH_3$ or $OC_2H_5$; and $Z_5$ to $Z_7$ each represents H, F, Cl, Br, OH, $NO_2$, CN or $CF_3$, provided that $Z_5$, $Z_6$ and $Z_7$ do not represent H at the same time.

n represents an integer of from 1 to 6; m represents an integer of from 1 to 5; and * represents a chiral center.

According to a further embodiment of the present invention, there is provided a liquid crystal display device including a pair of transparent substrates; a liquid crystal layer provided between the pair of substrates and having filled therein the liquid crystal molecules according to the embodiment of the present invention which display a smectic A phase where they are uniaxially aligned; and electrodes provided on the substrates, wherein a transmittance of the liquid crystal layer is regulated by inclining a longitudinal axis of the liquid crystal molecules through impression of an electric field on the liquid crystal layer from the electrodes.

According to a yet another embodiment of the present invention, there is provided a liquid crystal optical spatial modulation device including a pair of transparent substrates; a liquid crystal layer provided between the pair of substrates and having filled therein the liquid crystal molecules according to the embodiment of the present invention which display a smectic A phase where they are uniaxially aligned; and electrodes provided on the substrates, wherein spatial modulation regarding light transmitting through the liquid crystal layer is carried out by impressing an electric field on the liquid crystal layer from the electrodes.

In accordance with the embodiments of the present invention, there is provided a liquid crystal molecule displaying a smectic A phase as a liquid crystal molecule in a temperature range for use and having a large tilt angle in an electroclinic effect, from which sufficient optical modulation for use in a liquid crystal display device and a liquid crystal optical spatial modulation device is obtainable.

In accordance with the embodiments of the present invention, there is provided a liquid crystal display device which is excellent in dynamic image display quality, bright and high in gradation properties and contrast. For example, the liquid crystal display device is applicable to a direct view type LCD or a projection display micro liquid crystal device (for example, LCoS (liquid crystal on silicon) and high-temperature polysilicon TFT-LCD). Also, in particular, it is possible to realize a color display device by field sequential driving using color sequential backlight illumination.

In accordance with the embodiments of the present invention, there is provided a high-speed optical spatial modulation device capable of achieving three-dimensional display and the like.

DESCRIPTION OF THE PREFERRED EMBODIMENTS

<Liquid Crystal Molecule>

A liquid crystal molecule according to an embodiment of the present invention is hereunder described.

First of all, the liquid crystal molecule according to the embodiment of the present invention has a structure represented by the following general formula (1).

In the general formula (1), $X_1$ is a group selected among groups represented by the following formula (2).

In the general formula (1), $X_2$ is represented by the following formula (3).

In the formulae (1) to (3), $R_1$ represents a linear or branched hydrocarbon group or an alkoxy group each having from 4 to 16 carbon atoms; $R_2$ represents an optionally branched organosiloxane or organosilane having from 1 to 6 silicon atoms; and $R_3$ and $R_4$ are different from each other and each represents H, F, Cl, Br, CN, $CH_3$, $CF_3$ or $OCH_3$.

$Y_1$ represents -, —COO—, —$CH_2$—, —$CH_2O$—, —$C_2H_2$—, —$C_2$— or —$CF_2O$—.

$Z_1$ to $Z_4$ each represents H, F, Cl, Br, OH, $NO_2$, CN, $CF_3$, $CH_3$, $C_2H_5$, $OCH_3$ or $OC_2H_5$; $Z_5$ to $Z_7$ each represents H, F, Cl, Br, OH, $NO_2$, CN or $CF_3$, provided that $Z_5$, $Z_6$ and $Z_7$ do not represent H at the same time.

n represents an integer of from 1 to 6; * represents a chiral center; and - means a connecting group.

From the viewpoints of chemical stability of a molecular structure and thermal stability of a liquid crystal phase, a number of the silicon atom which is contained in the organosilane or organosiloxane structure is preferably from 1 to 6. Furthermore, a linear structure containing from 1 to 6 silicon atoms is preferable.

The liquid crystal molecule having such a structure displays a tilt angle of 30° or more and has a transmittance of 75% or more.

Also, it is more preferable that the liquid crystal molecule according to the embodiment of the present invention has a structure represented by the following general formula (4).

In the general formula (4), $X_2$ is represented by the following formula (3).

(3)

In the formulae (3) and (4), $R_{11}$ represents a linear or branched alkoxy group having from 4 to 16 carbon atoms; and $R_{13}$ represents F, Cl, Br, CN, $CH_3$, $CF_3$ or $OCH_3$.

$Z_1$ to $Z_4$ each represents H, F, Cl, Br, OH, $NO_2$, CN, $CF_3$, $CH_3$, $C_2H_5$, $OCH_3$ or $OC_2H_5$; and $Z_5$ to $Z_7$ each represents H, F, Cl, Br, OH, $NO_2$, CN or $CF_3$, provided that $Z_5$, $Z_6$ and $Z_7$ do not represent H at the same time.

n represents an integer of from 1 to 6; m represents an integer of from 1 to 5; and * represents a chiral center.

Here, the liquid crystal molecule according to the embodiment of the present invention forms a smectic liquid crystal layer and preferably displays a smectic A phase in a temperature region where a liquid crystal displayer device or a liquid crystal optical spatial device is used, for example, from 20 to 50° C. The smectic liquid crystal layer is a liquid crystal layer in which the longitudinal axis directions of the liquid crystal molecules are aligned in a layer form (smectic layer). The term "smectic A phase" as referred to herein means that in such a liquid crystal layer, the normal line direction of the liquid crystal layer coincides with the longitudinal axis direction of the liquid crystal molecules.

<Liquid Crystal Display Device>

Next, a configuration of a liquid crystal display device according to the embodiment of the present invention is described. The liquid crystal display device as referred to herein means a so-called direct view type display device such that the display device using a liquid crystal material is viewed directly by a viewer.

Figure 1:
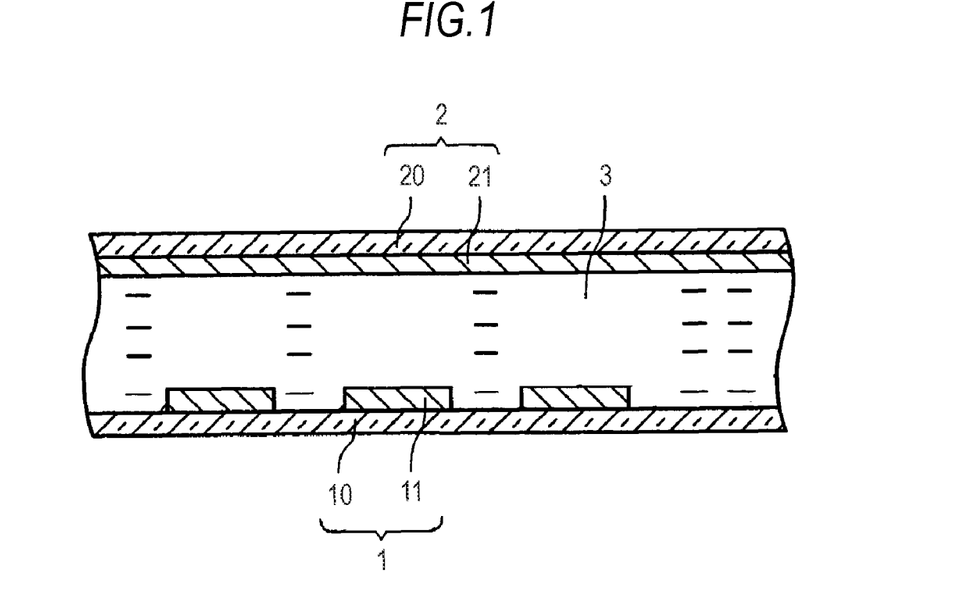
FIG. 1 is a sectional view showing a configuration of a liquid crystal display device according to an embodiment of the present invention.

FIG. 1 is a sectional view showing a configuration of the liquid crystal display device according to the embodiment of the present invention. Here, a principal part of a transmission type liquid crystal display device is shown, and an active matrix driving system by thin film transistor (TFT) driving is adopted as a driving system thereof.

As shown in FIG. 1, as a TFT array substrate 1, a TFT for switching is formed for each of a plurality of pixels disposed in a matrix pattern on one surface of a first substrate 10, and a pixel electrode 11 composed of a transparent electrode film connected thereto, such as an ITO film, is configured. Alternatively, a circuit for selecting other pixel or the like may be used in place of the TFT for switching. At that time, a dielectric film may be formed on the pixel electrode 11. Also, as a counter substrate 2, a non-illustrated color filter is formed on one surface of a second substrate 20 as the need arises, and a counter electrode 21 is formed so as to entirely cover them. Furthermore, non-illustrated retardation plates or polarizing plates or the like are formed at necessary locations of the TFT array substrate 1 and the counter substrate 2.

The TFT array substrate 1 and the counter substrate 2 are stuck to each other with a sealing material, and a liquid crystal layer 3 composed of a liquid crystal mixture (liquid crystal material) including the liquid crystal molecule according to the embodiment of the present invention is sealed in a gap between the TFT array substrate 1 and the counter substrate 2 via a non-illustrated alignment film and interposed therebetween. At that time, the liquid crystal molecules according to the embodiment of the present invention display a smectic A phase where the liquid crystal molecules are uniaxially aligned.

In the foregoing liquid crystal display device, a backlight unit such as an LED is provided on the back side. The transmission of light from the backlight unit can be regulated by varying the inclination (tilt angle) of the liquid crystal molecule by a voltage to be impressed between the pixel electrode 11 and the counter electrode 21 (by an electroclinic effect) to control a transmittance. Thus, in the liquid crystal display device according to the embodiment of the present invention, an image with gradation can be displayed.

As for a driving system in relation to an image signal, for example, a 1H reversal driving system (H means a horizontal scanning period) or a 1F reversal driving system (F means a field) or the like can be adopted. In such alternating current driving, the color level (gradation) of the liquid crystal can be varied by a height (magnitude of amplitude) of a driving voltage. In particular, at that time, the contrast of an image to be displayed can be further increased by increasing the driving voltage.

In the liquid crystal display device according to the embodiment of the present invention, since the liquid crystal molecule according to the embodiment of the invention is used, it is possible to display an image which is excellent in dynamic image display quality, bright and high in gradation properties and contrast.

<Liquid Crystal Optical Spatial Modulation Device>

Next, a configuration of a liquid crystal optical spatial modulation device according to an embodiment of the present invention is described.

The liquid crystal optical spatial modulation device as referred to herein means a device for planarly splitting light from a light source and varying the intensity, phase or the like of each of the individual light beams thus obtained. This liquid crystal optical spatial modulation device includes a micro-display (LCoS) or light valve used in a projector display, or a phase modulation device such as a light deflection switch. As a specific example of the light valve, the liquid crystal display device shown in FIG. 1 may be applied. That is, light emitted from a light source is separated into red, green and blue rays, the respective color rays are modulated by three light valves, each of which is configured of the liquid crystal display device according to the embodiment of the present invention, and the thus modulated color light beams are again synthesized, thereby achieving enlarged projection on a projection surface.

Figure 2:
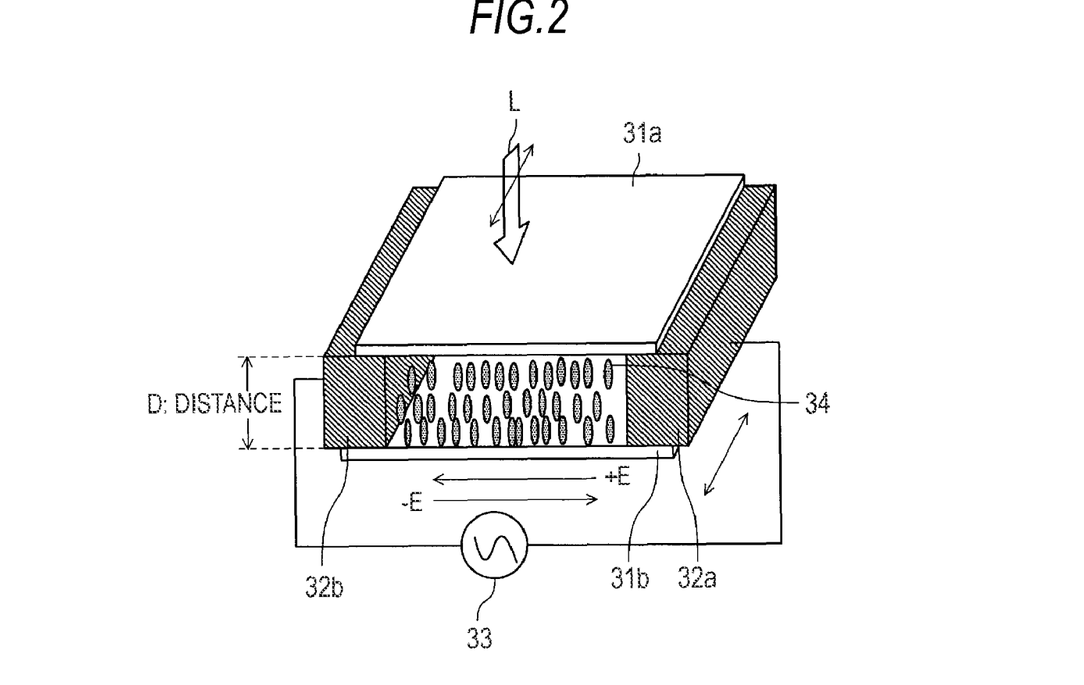
FIG. 2 is a diagrammatic view showing a configuration of a liquid crystal optical spatial modulation device according to an embodiment of the present invention.

FIG. 2 shows a configuration example of a light deflection switch as the liquid crystal optical spatial modulation device according to the embodiment of the present invention.

As shown in FIG. 2, a pair of transparent substrates 31a and 31b made of a glass or the like is disposed such that their principal surfaces are made parallel and opposing to each other with a predetermined spacing, and the opposing surfaces are coated with a vertical aligning agent for vertically aligning the liquid crystal molecules. Also, electrodes 32a and 32b are clamped between the transparent substrates 31a and 31b at both ends thereof in one direction, and an alternating current field is impressed between the electrodes 32a and 32b from an external driving unit 33 for impressing an alternating current field.

Liquid crystal molecules 34 according to the embodiment of the present invention are sealed between the transparent substrates 31a and 31b. The liquid crystal molecules 34 display a smectic A phase in the use environment for the liquid crystal optical spatial modulation device and are aligned vertically to the principal surfaces of the transparent substrates 31a and 31b in a state where an electric field is not impressed by the action of the vertical aligning agent.

In the liquid crystal optical spatial modulation device, an incident light L is made incident in parallel to the normal line of the substrate (vertically to the substrate) from the side of the substrate 31a. The incident light L is deflected by an electric field to be impressed between the electrodes 32a and 32b into a direction orthogonal to the electric field direction and then emitted. For example, when an electric field E is 0, shifting of the incident light is not generated, whereas when the electric field E is more than 0, the incident light is deflected and shifted into a prescribed direction (+ direction) orthogonal to the electric field direction and then emitted. Also, when the electric field E is less than 0, the incident light is deflected and shifted into a reverse direction (− direction) to the direction in the case where the electric field E is more than 0 and then emitted. Also, a shifting amount thereof can be regulated by the intensity of the electric field.

EXAMPLES

Embodiments according to the present invention are more specifically described below with reference to the following Examples.

Example 1

6-{[(R)-1-Methyl-5-(1,1,3,3,3-pentamethyldisiloxanyl)hexyl]-oxy}-5-nitronaphthyl-2-yl 4-(dodecyloxy)benzoate (1) Synthesis of Liquid Crystal Molecule:

A liquid crystal molecule of an embodiment according to the present invention was obtained by the following procedures.

After adding dropwise benzoyl chloride to a pyridine solution of 2,6-naphthol, the mixture was stirred at room temperature overnight, and the thus obtained deposit was filtered and subjected to column chromatography with a silica gel to obtain 6-hydroxy-2-naphthyl benzoate.

The thus obtained 6-hydroxy-2-naphthyl benzoate was dispersed in acetic acid, nitric acid was added dropwise to the dispersion while keeping it at 15° C., and water was further added thereto, followed by stirring. The thus obtained deposit was recrystallized from ethanol/acetic acid to obtain 6-hydroxy-5-nitro-2-naphthyl benzoate.

An argon-purged flask was charged with the thus obtained 6-hydroxy-5-nitro-2-naphthyl benzoate, triphenylphosphine and a tetrahydrofuran (THF) solution of (S)-5-hepten-2-ol, a THF solution of diethyl azodicarboxylate was added dropwise thereto, and the mixture was stirred at room temperature overnight. After evaporating off the solvent, the residue was subjected to column chromatography to obtain 6-{[(R)-1-methyl-4-hexenyl]oxy}-5-nitronaphthyl-2-yl benzoate.

A lithium hydroxide aqueous solution was added to a methanol solution of the thus obtained 6-{[(R)-1-methyl-4-hexenyl]oxy}-5-nitronaphthyl-2-yl benzoate, and the mixture was stirred at room temperature overnight. After evaporating off the solvent, the residue was neutralized with hydrochloric acid, and a desired material was extracted with ethyl ether. After dehydrating the extract with magnesium sulfate, the solvent was evaporated off, and the residue was subjected to column chromatography to obtain 6-{[(R)-1-methyl-4-hexenyl]oxy}-5-nitronaphthyl-2-ol.

The thus obtained 6-{[(R)-1-methyl-4-hexenyl]oxy}-5-nitronaphthyl-2-ol, p-dodecaoxybenzoic acid and a dichloromethane solution of 4-dimethylaminopyridine were added to 1-(3-(dimethylamino)-propyl)-3-ethylcarbodiimide methiodine, and the mixture was stirred at room temperature overnight. After washing the solution with water, the resulting solution was subjected to liquid separation and then dried over sodium sulfate. After evaporating off the solvent, the residue was subjected to column chromatography to obtain 6-{[(R)-1-methyl-4-hexenyl]oxy}-5-nitronaphthyl-2-yl 4-(dodecyloxy)benzoate.

Dichloro(dicyclopentadienyl)platinum(II) as a catalyst was added to the thus obtained 6-{[(R)-1-methyl-4-hexenyl]oxy}-5-nitronaphthyl-2-yl 4-(dodecyloxy)benzoate and a THF solution of 1,1,3,3,3-pentamethyldisiloxane, and the mixture was stirred in an argon atmosphere at 60° C. for 24 hours. After evaporating off the solvent, the residue was subjected to column chromatography to obtain 6-{[(R)-1-methyl-5-(1,1,3,3,3-pentamethyldisiloxanyl)hexyl]-oxy}-5-nitronaphtyl-2-yl 4-(dodecyloxy)benzoate (final product 1). A structural formula of each of this final product 1 and final products 2 to 4 as described later is shown below.

Figure 3:
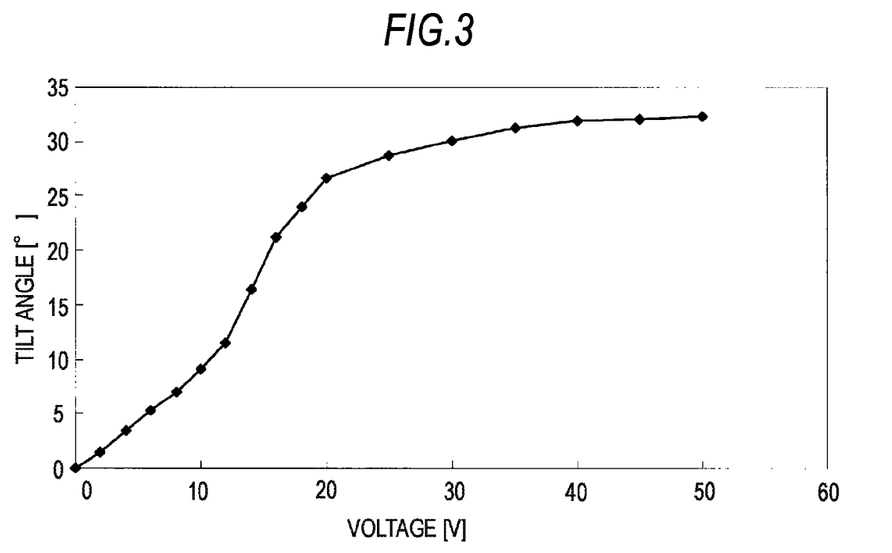
FIG. 3 is a diagram showing the relationship between a voltage and a tilt angle of an evaluation cell of Example 1.

The final product 1 displayed a smectic A phase at from 30° C. to 48° C. The dependency of a tilt angle thereof on the impressed voltage is shown in FIG. 3.

Determination of the phase transition temperature and identification of the smectic A phase were carried out by means of differential scanning calorimetry and polarizing microscope observation with a hot stage.

(2) Preparation of Evaluation Cell:

After fabricating a polyimide alignment film on a glass substrate provided with ITO (indium tin oxide), the film was rubbed by a buffed roller, and a cell was prepared by use of an ultraviolet ray-curable resin having dispersed therein silica balls with a diameter of 2.4 μm. Subsequently, the liquid crystal molecule (final product 4) synthesized by the foregoing method was poured into the cell at a temperature for promising an isotropic phase, thereby forming an evaluation cell.

(3) Evaluation of Evaluation Cell:

The thus obtained evaluation cell was evaluated as to a maximum tilt angle, a transmittance and a response time.

As to the maximum tilt angle, the evaluation cell was disposed between orthogonal polarizing plates, a transmitted light quantity was measured while impressing a rectangular wave electric field on the cell, and a half of the angle formed between an optical axis of the polarizing plate and an optical axis of the evaluation cell at which a minimum light quantity was given in positive- and negative-polarity electric fields, respectively was designated as a tilt angle.

Also, as to the transmittance, an optical axis of the evaluation cell at the time of impressing no electric field was set so as to coincide with an optical axis of a polarizing plate of a polarizing microscope, a transmitted light quantity upon impressing an electric field giving a maximum tilt angle was measured by a spectrophotometer, and the transmittance was calculated by taking a value with parallel polarizing plate arrangement as 100%.

Also, as to the response time, the same optical disposition as that for the measurement of a transmittance was used, and a rise time in the case where a voltage was impressed stepwise from a zero electric field so as to give a maximum tilt angle was taken as the response time.

Example 2

6-{[(R)-1-Methyl-4-(1,1,3,3,3-pentamethyldisiloxanyl)heptyl ]-oxy}-5-nitronaphthyl-2-yl 4-(dodecyloxy)benzoate Synthesis was carried out in the same manner as in Example 1, except for using (S)-4-octen-2-ol in place of the (S)-5-hepten-2-ol, thereby obtaining 6-{[(R)-1-methyl-4-(1,1,3,3,3-pentamethyldisiloxanyl)heptyl ]-oxy}-5-nitronaphthyl-2-yl 4-(dodecyloxy)benzoate (final product 2).

Figure 4:
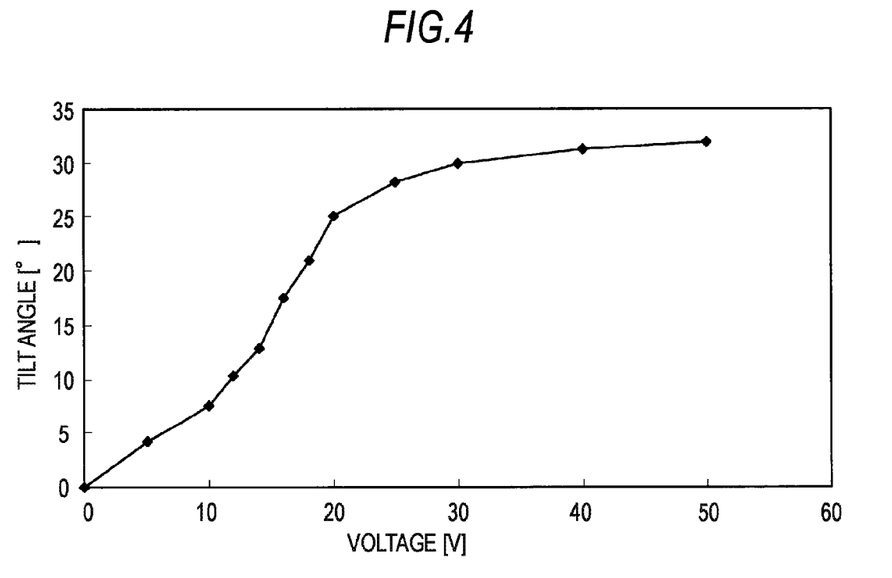
FIG. 4 is a diagram showing the relationship between a voltage and a tilt angle of an evaluation cell of Example 2.

The final product 2 displayed a smectic A phase at from 32° C. to 52° C. The dependency of a tilt angle thereof on the impressed voltage is shown in FIG. 4.

Comparative Example 1

5-Nitro-6-[(1S)-1-methylhexyloxy]naphthyl-2-yl 4-(6-pentamethyldisiloxyhexyloxy)benzoate Synthesis was carried out in the same manner as in Example 1, except for using 4'-(5-hexenyloxy)benzoic acid in place of the p-dodecaoxybenzoic acid and (S)-2-heptanol in place of the (S)-5-hepten-2-ol, respectively, thereby obtaining 5-nitro-6-[(1S)-1-methylhexyloxy]naphthyl-2-yl 4-(6-pentamethyldisiloxyhexyloxy)benzoate (final product 3).

The final product 3 displayed a smectic A phase at from 29° C. to 35° C. However, according to such an alignment method, a uniform monodomain was not obtained, and the electro-optic measurement of a tilt angle and the like could not be achieved.

Comparative Example 2

4-{3'-Nitro-4'-[(1S)-1-methylhexyloxy]phenyl}phenyl 4-(6-pentamethyldisiloxyhexyloxy)benzoate Synthesis was carried out in the same manner as in Comparative Example 1, except for using p,p'-biphenol in place of the 2,6-naphthol, thereby obtaining 4-{3'-nitro-4'-[(1S)-1-methylhexyloxy]phenyl}phenyl 4-(6-pentamethyldisiloxyhexyloxy)benzoate (final product 4).

Figure 5:
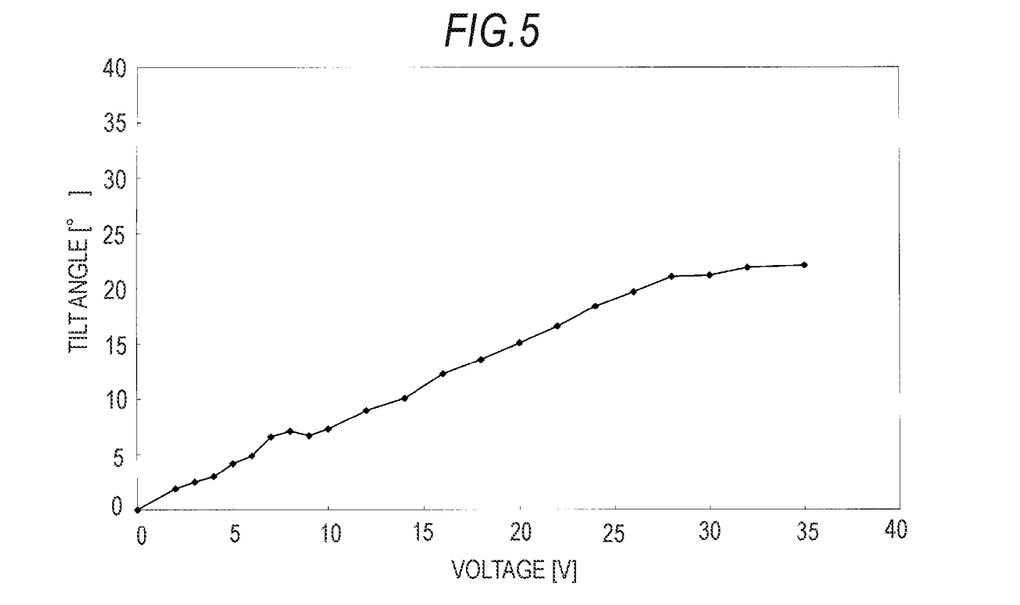
FIG. 5 is a diagram showing the relationship between a voltage and a tilt angle of an evaluation cell of Comparative Example 2.

The final product 4 displayed a smectic A phase at from 38° C. to 55° C. The dependency of a tilt angle thereof on the impressed voltage is shown in FIG. 5.

Results of the evaluation (measured values of maximum tilt angle and transmittance on that occasion) of Examples 1 to 2 and Comparative Examples 1 to 2 are shown in Table 1. Response times were all from 50 μseconds to 100 μseconds, and there was not admitted a significant difference exclusive of Comparative Example 1 in which the measurement could not be achieved.

TABLE 1

|  | Example 1 | Example 2 | Comparative Example 1 | Comparative Example 2 |
|---|---|---|---|---|
| Maximum tilt angle | 33° | 32° | Could not be measured | 22° |
| Transmittance | 83% | 81% | Could not be measured | 47% |

As is clear from the comparison of Examples 1 to 2 with Comparative Example 1, in the case where a core portion having a plurality of aromatic groups including a naphthylene group is present in one end of an asymmetric carbon atom, and a siloxane is added to the core portion, uniform alignment is not obtained by means of polyimide rubbing alignment which is generally adopted, resulting in producing a very serious problem in mass production.

Also, in the case of Comparative Example 2 in which a core portion having a plurality of aromatic groups in one end of an asymmetric carbon atom is present, and a siloxane is added to the core portion, the maximum tilt angle is only 22°, and the transmittance is less than 50%, values of which are not utterly endurable to practical use. In the case of LCD, power consumption is mostly by backlight, and a liquid crystal material through which only less than a half of the light quantity can transmit produces a serious problem on practical usage.

On the other hand, in all of the compounds of Examples 1 and 2 having a structure having an asymmetric carbon atom and having a core portion including a naphthylene group containing a functional group and an organosilane or an organosiloxane at positions opposite to each other interposing the asymmetric carbon atom therebetween, the tilt angle is 30° or more, and the corresponding transmittance is 75% or more.

The present application contains subject matter related to that disclosed in Japanese Priority Patent Application JP 2008-261261 filed in the Japan Patent Office on Oct. 8, 2008, the entire contents of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A liquid crystal molecule having a structure represented by the following general formula (1):

wherein $X_1$ is a group selected among groups represented by the following formula (2):

$X_2$ is represented by the following formula (3):

$R_1$ represents a linear or branched hydrocarbon group or an alkoxy group each having from 4 to 16 carbon atoms;

$R_2$ represents an optionally branched organosiloxane or organosilane having from 1 to 6 silicon atoms;

$R_3$ and $R_4$ are different from each other and each represents H, F, Cl, Br, CN, $CH_3$, $CF_3$ or $OCH_3$;

$Y_1$ represents -, —COO—, —$CH_2$—, —$CH_2O$—, —$C_2H_2$—, —$C_2$— or —$CF_2O$—;

$Z_1$ to $Z_4$ each represents H, F, Cl, Br, OH, $NO_2$, CN, $CF_3$, $CH_3$, $C_2H_5$, $OCH_3$ or $OC_2H_5$;

$Z_5$ to $Z_7$ each represents H, F, Cl, Br, OH, $NO_2$, CN or $CF_3$, provided that $Z_5$, $Z_6$ and $Z_7$ do not represent H at the same time;

n represents an integer of from 1 to 6;

* represents a chiral center; and

- means a connecting group.

2. A liquid crystal molecule having a structure represented by the following general formula (4):

wherein $X_2$ is represented by the following formula (3):

$R_{11}$ represents a linear or branched alkoxy group having from 4 to 16 carbon atoms;

$R_{13}$ represents F, Cl, Br, CN, $CH_3$, $CF_3$ or $OCH_3$;

$Z_1$ to $Z_4$ each represents H, F, Cl, Br, OH, $NO_2$, CN, $CF_3$, $CH_3$, $C_2H_5$, $OCH_3$ or $OC_2H_5$;

$Z_5$ to $Z_7$ each represents H, F, Cl, Br, OH, $NO_2$, CN or $CF_3$, provided that $Z_5$, $Z_6$ and $Z_7$ do not represent H at the same time;

n represents an integer of from 1 to 6;

m represents an integer of from 1 to 5; and

* represents a chiral center.

3. A liquid crystal display device comprising:

a pair of transparent substrates;

a liquid crystal layer provided between the pair of substrates and having filled therein the liquid crystal molecules according to claim 1 or 2, which display a smectic A phase where they are uniaxially aligned; and electrodes provided on the substrates, wherein a transmittance of the liquid crystal layer is regulated by inclining a longitudinal axis of the liquid crystal molecules through impression of an electric field on the liquid crystal layer from the electrodes.

4. A liquid crystal optical spatial modulation device comprising:

a pair of transparent substrates;

a liquid crystal layer provided between the pair of substrates and having filled therein the liquid crystal molecules according to claim 1 or 2, which display a smectic A phase where they are uniaxially aligned; and electrodes provided on the substrates, wherein spatial modulation regarding light transmitting through the liquid crystal layer is carried out by impressing an electric field on the liquid crystal layer from the electrodes.

* * * * *